United States Patent [19]

Bredael et al.

[11] 4,004,165
[45] Jan. 18, 1977

[54] ULTRASONIC SIGNAL GENERATORS

[75] Inventors: Ivo Leo Bredael, Ispra, Varese; Fulvio Laghi, Varese, both of Italy

[73] Assignee: European Atomic Energy Community (Euratom), Kirchberg, Luxembourg

[22] Filed: July 7, 1975

[21] Appl. No.: 593,212

Related U.S. Application Data

[63] Continuation of Ser. No. 454,850, March 26, 1974, abandoned.

[30] Foreign Application Priority Data

Mar. 27, 1973 United Kingdom ............ 14735/73

[52] U.S. Cl. ................................................ 310/8.1
[51] Int. Cl.² ...................................... H01L 41/04
[58] Field of Search ..................... 310/8.1, 8.4; 73/67.8 R, 67.8 S, 67.9, 71.4, 69; 340/15, 17

[56] References Cited

UNITED STATES PATENTS

| | | | |
|---|---|---|---|
| 3,125,295 | 3/1964 | Moss et al. ........................ | 310/8.1 X |
| 3,282,068 | 11/1966 | McCorkindale et al. ........... | 73/67.8 |
| 3,328,609 | 6/1967 | Clicques ............................ | 310/8.1 |
| 3,405,288 | 10/1968 | Dittrich et al. .................... | 310/8.4 |
| 3,569,747 | 3/1971 | Siegel ................................ | 310/8.4 X |
| 3,604,250 | 9/1971 | Grandia ............................ | 73/67.8 |
| 3,620,070 | 11/1971 | Collins .............................. | 73/67.8 |

FOREIGN PATENTS OR APPLICATIONS

| | | | |
|---|---|---|---|
| 1,525,998 | 2/1967 | France .............................. | 310/8.1 |
| 849,096 | 9/1960 | United Kingdom | |

*Primary Examiner*—Mark O. Budd
*Attorney, Agent, or Firm*—Stevens, Davis, Miller & Mosher

[57] ABSTRACT

A piezo electric signal generator and receiver assembly for a flaw detector has a generator adjacent to the crystal transducer and a cable connection to a distant point where a d.c. power supply and the indicator is located. The same cable is used for supplying power to the generator and for conveying to the indicator signals corresponding to both acoustic transmitted pulses and reflected returns. For this purpose a charging voltage is applied to a series circuit comprising the capacitor and crystal and this circuit is discharged by a switch connected to the capacitor at the input end of the charging circuit. Both transmitted and received signals are fed in the same direction through the cable and are therefore subjected to the same delays.

1 Claim, 2 Drawing Figures

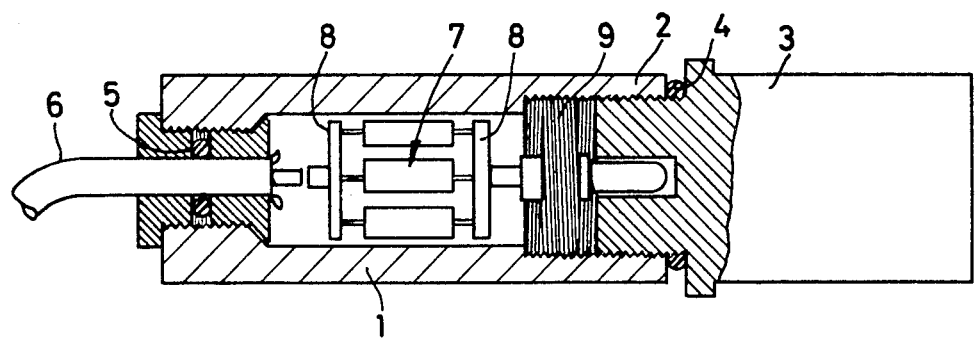
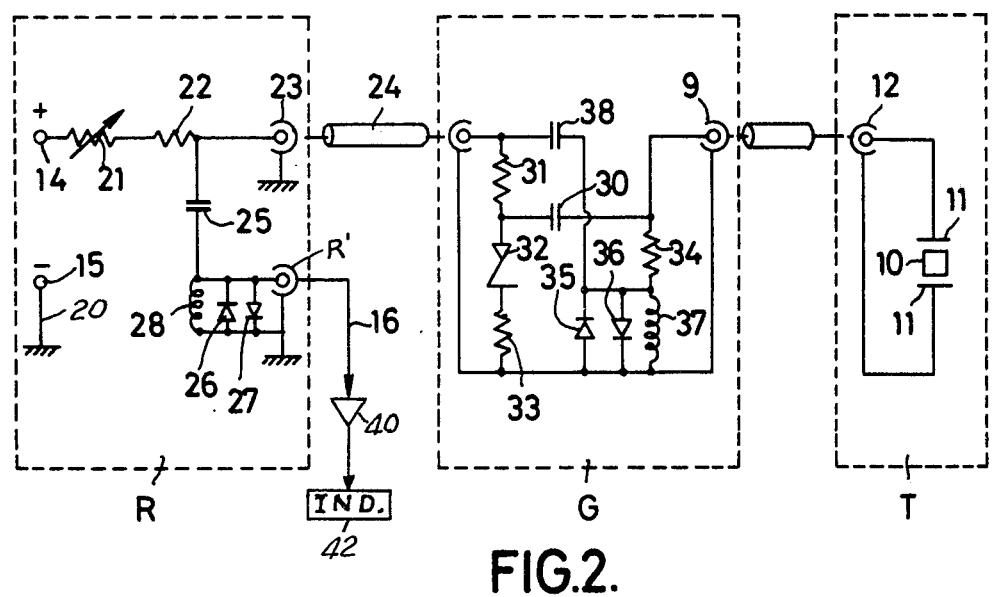

ULTRASONIC SIGNAL GENERATORS

This is a continuation of application Ser. No. 454,850 filed Mar. 26, 1974, now abandoned.

BACKGROUND OF THE INVENTION

1. Field of the Invention

This invention relates to an ultrasonic signal generator making use of a piezo electric transducer.

2. Prior Art

Such a signal generator is used for example in a flaw detector. The piezo electric transducer is connected to a pulse generator and it is well known to use, as the generator, a capacitor and a switch which discharges the capacitor into the load formed by the transducer. Such an arrangement is shown, for example, in French Patent Specification No. 1525998. The generator must include means by which reflected signals picked up by the transducer and converted thereby to electric signals are fed to a receiver. It is commonly necessary for the measuring instrumentation to be remote from the point to be examined and thus heretofore it has often been necessary to feed the transducer through a relatively long cable from the generator. Although for many purposes, a long cable can be successfully used, the cable losses limit the length which can be used while still obtaining sufficient power to be applied to the transducer. The greater the cable length, the larger the power required and hence the need for a bulky and expensive generator. Moreover signal distortions arise due to reflections at the mismatches introduced by the cable. As is well known, the mismatch from the generator to the cable is mostly due to the variation of the negative resistance of the switch and to the nonlinearity of the other components which arise because of the high voltage and current stresses created during the pulse generation. At the transducer end of the cable, there is a mismatch between the cable and the transducer which is time dependent; at the beginning of the pulse the transducer acts as a capacitor because its electrodes are stationary and at this stage, therefore all the incident power is reflected back through the cable to the generator with an apparent source impedance of about zero ohms and a phase shift of about 180° depending on the rate of the rise of the voltage. The losses are resistive if no coil or transformer is used (which would reduce the crystal damping factor, restrict the band pass and might introduce a parasitic secondary oscillation).

SUMMARY OF THE INVENTION

It is an object of the present invention to provide an improved form of piezo electric signal generator which avoids or minimizes these problems.

According to the present invention a piezo electric signal generator and receiver assembly comprises a piezo electric crystal transducer, a generator arranged adjacent to the transducer and electrically connected thereto, said generator comprising a capacitor in series with the piezo electric crystal, an input to the generator for applying a charging voltage to the series circuit comprising the capacitor and crystal, a switch connected to said capacitor at the input end of the charging circuit for discharging the series circuit, and circuit means connected to the junction of the capacitor and crystal and including a voltage limiter and capacitive coupling means connecting the voltage limiter to said input terminal.

With the above described piezo electric signal generator, the input terminal of the generator can be connected by a relatively long cable to a direct voltage power supply constituting said power source. This power source can be connected to the cable through a blocking resistor and the junction of the cable and blocking resistor may be capacitively coupled to a pulse amplifier which may feed a receiver. It will be seen that when the switch is closed in the generator to discharge the series circuit, the voltage across the crystal is suddenly changed thereby giving the required pulse excitation for generating an ultrasonic pulse signal. A small part of the pulse energy, limited by the limiter circuit will be transmitted back through the aforementioned cable to the amplifier at the receiver end of the cable. Assuming that the transducer is used in a flaw detector, subsequent reflected signals picked up by the crystal will likewise be applied to the limiter (although this amplitude may be below the limiting level) and will pass through the cable to the amplifier. It will be noted that the length of the cable no longer constitutes a limitation on the rise time or amplitude of the initial pulse signal applied to the crystal or on the ultrasonic signal output from the crystal. The signal corresponding to the applied pulse from the transducer and the received reflections in a flaw detector pass through the connecting cable in the same direction from the aforementioned limiter circuit to the receiver and thus are affected in the same way by any changes in cable length or temperature changes. The connecting cable may conveniently be a coaxial cable which carries these pulse signals and also the D.C. power supply. This power supply typically may be a 250 V 0.5 mA supply source.

The switch is conveniently constituted by a switching device operating when the voltage on the capacitor reaches a predetermined value thereby forming a selfrunning relaxation circuit producing repetitive pulses. For this purpose the switching device may be for example a four layer diode or a thyristor operating in the break-down voltage zone.

The aforementioned blocking resistor at the receiver end of the cable conveniently includes an adjustable resistor in series with the DC power supply for permitting adjustment of the pulse repetition rate.

The aforesaid voltage limiter for feeding reflected signals to the cable conveniently comprises a pair of limiting diodes connecting in shunt back to back with a D.C. restoring coil connected in shunt across these limiting diodes. The limiting circuit is preferably connected, in series with a resistor, across the crystal, the resistor being of a magnitude to match the impedance of the cable connection between the generator and the supply source. This connection may conveniently be coaxial connection of for example 50 ohms impedance.

Preferably a resistor is connected in series with the switch having a positive resistance substantially matching the negative dynamic resistance of the crystal. This is not critical, and in a typical case, where the crystal has a negative dynamic resistance of 4 ohms, a 10 ohms series resistance which is used in series with the switch as a current limiting resistor gives adequate matching in this respect.

Physically the piezo electric crystal transducer is preferably mounted directly on a support containing the generator and detector circuit. For example the support may be of tubular form threaded at one end to receive a threaded end of a piezo electric transducer, the transducer having a suitable connecting socket mating with a connecting element within the tube for effecting the electrical connection.

With this arrangement, when the switch is closed, and the voltage applied to the crystal electrodes is suddenly changed, the crystal begins to move under the piezo electric action and this induces an emf which is delayed with respect to the driving pulse and which reduces the energy reflected back to the capacitor. The induced voltage has an inductive component and the crystal is acting as a small inductance. If the capacitor has a value such that, together with the inductance of the transducer, the whole circuit oscillates at the same frequency as the transducer, then the phase of the current in the electrical circuit and the current produced by the piezo electric crystal are in opposition and the displacement of the crystal is strongly damped, as is desirable to produce a short duration pulse.

BRIEF DESCRIPTION OF THE DRAWING

FIG. 1 is a diagrammatic sectional view of a piezo electric transducer with an associated generator and detector circuit constituting one embodiment of the invention; and FIG. 2 is an electrical circuit diagram showing the piezo electric transducer with the associated generator and detector circuit and the connecting cable to a power supply and receiver unit.

DESCRIPTION OF THE PREFERRED EMBODIMENT

Referring to FIG. 1, the generator and detector are housed within a tubular housing or support 1 which, by means of internally threaded end portion 2 accepts a screw thread on the end of a transducer 3, an O-ring seal 4 being provided between the tubular housing and the transducer to make a leak-proof joint. At the opposite end of the housing 1, a leak-proof joint 5 is provided around an electrical cable 6 which enters into the housing. The generator 7 is arranged within the housing and is mounted onto a printed circuit board 8. The electrical connection between the generator 7 and the transducer 3 is by means of a UHF plug and socket connection having the male connector 9 in the housing to engage with a socket in the transducer 3. In a typical example, the housing 1 is only 14 millimeters in internal diameter and 25 millimeters long. The transducer might typically be an alpha type Aerotech transducer operating in the range of 2.25 to 10 MHz, for example a 5 MHz transducer is indicated at T and is illustrated diagrammatically as comprising the crystal 10 with its electrodes 11 and a connector 12 providing a coaxial connection to the aforementioned male connector 9 in the generator which generator is indicated by the box G in FIG. 2. FIG. 2 also shows at R the transmit/receiver box having terminals 14, 15 for connection to a 250 V 0.5 mA DC power supply source and having an output terminal R' for connection by a lead 16 to a pulse amplifier having a 50 ohm input impedance. The amplifier may feed an indicator 42 or recorder. The negative terminal 15 of the power supply source is grounded as shown at 20 and the positive terminal is connected through an adjustable 1 Mohm resistor 21 and a 10 kohm blocking resistor 22 to an output terminal 23 for connection to the inner conductor of a coaxial cable 24 of 50 ohms impedance which extends between the transmit/receive box R and the generator G. This cable 24 typically might be an RG 58/u cable which, if one Kilometer long, would give a loss of only 30 dB which is easily compensated by the appropriate gain in the aforementioned amplifier. The cable end of the blocking resistor 22 is connected by means of a 47nFd coupling capacitor 25 to a limiter circuit comprising two limiting diodes 26, 27 connected in shunt between the coupling capacitor 25 and ground, the capacitor 25 being connected also to the aforementioned terminal leading to the amplifier. A 20 mH coil 28 is connected as a DC restorer across the limiting diodes.

In the generator, a capacitor 30 of 680 pFd is connected between the aforementioned male connector 9 leading to the transducer and a 150 kohms resistor 31 leading to the aforementioned coaxial cable 24. The capacitor 30 is of the non-microphonic type, that is to say it should have zero capacitance change with voltage variation, in order to avoid any introduction of ringing and parasitic oscillations from the capacitor. The junction of the capacitor 30 and 150 kohm resistor 31 is connected via a four layer diode 32 and a 10 ohm current limiting resistor 33 to the grounded outer conductor of the cable 24. The coupling circuit for coupling reflected signals to the cable comprises a 47 ohm resistor 34 connected to ground via a limiting circuit comprising two limiting diodes 35, 36 in shunt between the resistor 34 and ground, these diodes being shunted by a 1.5 mH coil 37 to give DC restoration. The junction of the resistor 34 and the limiting circuit is coupled by a 47 nFd capacitor 38 to the aforementioned coaxial cable 24.

When power is applied to the input terminals 14, 15, the capacitor 30 and crystal 10 charge through the 150 kohm resistor 31 in the generator and when the voltage on the capacitor 30 reaches about 200 V, the diode 32 breaks down and the capacitor 30 discharges through the diode 32 the 10 ohm limiting resistor 33 and the transducer 10. This discharge produces a peak current of about 5 amps. This discharge current is limited by the current limiting resistor 33 in series with the diode 32 which resistor limits the peak recurrent current of the diode of 8 amps. At the instant when the diode switch 32 closes and the capacitor 30 starts to discharge, the piezo electric crystal 10 acts as a capacitor. At this moment, that is the beginning of the power pulse, the electrodes of the crystal 10 are stationary and the 200 V in the series circuit is divided in the ratio of the capacities of the aforementioned capacitor 30 and crystal 10, giving, in this particular embodiment, about 70 V on the crystal 10 which has a capacity of 1500 pFd. The crystal 10 begins to move, inducing an emf which is delayed with respect to the driving pulse. This emf reduces the reflected energy to the capacitor 30. This is because the induced voltage has an inductive component and the crystal is acting as a small inductance. The capacitor 30 has a value such that, together with this inductance of the transducer 10, it gives a resonant frequency for the circuit which is the same as the frequency of the resonance frequency of the crystal transducer. The phase of the current in this electric circuit and of that produced by the crystal are in opposition and thus the piezo electric displacement of the crystal is strongly damped. These considerations lead to the choice of the magnitude of the capacitor. This magnitude is not critical and for example a 10% error is not of any importance because the bandwidth of the transducer would be at least as broad as 10%.

The current limiting resistor 33 of 10 ohms has a magnitude determined by the required current limit but substantially matches the negative dynamic resistance of the crystal which might typically be of the order of 4 ohms.

In the coupling circuit, the limiting diodes 35, 36 limit the peak voltage to about 1.5 V during the time of the applied pulse. The 1.5 mH coil 37 restores the DC mismatch between the two limiting diodes 35, 36 and gives a low impedance for the charging current of the capacitor 30 during the receive period. At the transducer 10, any reflected signals will give rise to pulse signals which are applied to the cable by the coupling capacitor 38 which has, at 5 MHz, a reactance of 0.6 ohms; this reactance is negligible compared with the cable impedance. The 47 ohm resistor 34 thus provides the matching to the impedance of cable 24.

The maximum repetition rate with this circuit will depend on the ambient temperature and, in this particular embodiment is about 6 kHz at 50° C or 4kHz at 125° C for 10% component tolerances. In a typical application, the transducer 10 is arranged in water on an aluminum reflector and the signal received from the transducer might be 700 mV or greater peak to peak at 5MHz. The time position of this reflected signal related to the transmitted pulse is independent of the length of the cable 24 because the transmitted pulse is also applied to the cable (via the limiter 35, 36). The transmitted pulses and reflected pulses thus pass through the cable 24 in the same direction with the same velocity. This cable also provides the DC power supply connection to the generator. The length of cable thus does not introduce any limitation in the magnitude of the generated signal or the signal quality. With the arrangement described, the sensitivity is high because the impedances can be well matched. The ohmic losses of the transmission cable 24 are kept small by working with low current levels. The broad band frequency spectrum of the transducer is not distorted by parasitic oscillations originating in the circuit. The dissipated power is typically about 125 mW at 4 kHz repetition rate and is so small that it will not disturb the operation of the crystal by heating. It permits the use of light battery powered instruments to an ambient temperature of 125° C in liquids.

The impedance of the generator is readily matched to the characteristic impedance of the transmitting cable thereby facilitating long distance transmission. It will also be noted that the volume of the arrangement is so small that the generator can readily be enclosed in the normal housing of a piezo electric crystal. The generator is economic to make and its cost is only a small fraction of the transducer cost.

We claim:

1. In an ultrasonic flow detector of the kind comprising a piezoelectric crystal transducer, a pulse generator having capacitive means and switching means periodically discharging said capacitive means for generating repetitive voltage pulses for excitation of the transducer; a transmitting cable for the transmission of signals applied to and received from said transducer, said cable having a first end coupled to said transducer and a second end; a remote transmit/receive unit electrically connected to the second end of said cable and by said cable to said transducer, said remote transmit/receive unit comprising coupling means for connecting with a D.C. power source, pulse amplifier means for amplifying the signals received from the transducer, and indicator means for indicating the signals transmitted to and received from said transducer; the improvement wherein said pulse generator is closely connected to said transducer within the same housing to provide an oscillating unit, said pulse generator dissipates relatively low power, and said oscillating unit is connected to the first end of said transmitting cable; said capacitive means of said pulse generator has a reactance substantially equal to the reactance of said crystal transducer at the resonant frequency of said transducer; and said pulse generator includes resistive means having a magnitude matching the impedance of said cable to said transducer, and voltage limiting means, said resistive means and said voltage limiting means being coupled across said transducer.

* * * * *